United States Patent
Ortiz

(10) Patent No.: US 7,462,186 B2
(45) Date of Patent: Dec. 9, 2008

(54) ANASTOMOTIC RING APPLIER DEVICE UTILIZING AN ELECTROACTIVE POLYMER

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 427 days.

(21) Appl. No.: 11/120,854

(22) Filed: May 3, 2005

(65) Prior Publication Data

US 2006/0253135 A1 Nov. 9, 2006

(51) Int. Cl.
*A61B 17/10* (2006.01)

(52) U.S. Cl. ................................ 606/139; 606/153

(58) Field of Classification Search ................ 606/151, 606/153–157, 139
See application file for complete search history.

(56) References Cited

U.S. PATENT DOCUMENTS

| 5,853,422 | A * | 12/1998 | Huebsch et al. ............ 606/213 |
| 5,855,312 | A | 1/1999 | Toledano |
| 6,171,321 | B1 | 1/2001 | Gifford et al. |
| 6,249,076 | B1 | 6/2001 | Madden et al. |
| 6,451,029 | B1 | 9/2002 | Yeatman |
| 6,485,496 | B1 | 11/2002 | Suyker et al. |
| 2003/0032967 | A1 | 2/2003 | Park et al. |
| 2003/0065358 | A1 | 4/2003 | Frecker et al. |
| 2003/0069474 | A1 | 4/2003 | Couvillon, Jr. |
| 2005/0070921 | A1 * | 3/2005 | Ortiz et al. ................ 606/139 |
| 2005/0102017 | A1 * | 5/2005 | Mattison ................... 623/1.11 |
| 2005/0165439 | A1 * | 7/2005 | Weber et al. ............... 606/191 |

FOREIGN PATENT DOCUMENTS

EP 1520531 4/2005

OTHER PUBLICATIONS

Office Action dated Jan. 4, 2006, for U.S. Appl. No. 10/675,497, filed Sep. 30, 2003.
European Search Report, dated Sep. 18, 2006, for EP Application No. 06252334.5.

* cited by examiner

*Primary Examiner*—Todd E Manahan
*Assistant Examiner*—Jennifer L Hornberger
(74) *Attorney, Agent, or Firm*—Frost Brown Todd LLC

(57) ABSTRACT

A surgical instrument is operable to deploy an anastomotic ring device. The instrument comprises a ring deployment mechanism configured to receive and deploy the anastomotic ring through an actuating force. The instrument further comprises an electroactive polymer that is configured to receive voltage from a power source. The electroactive polymer is configured to convert the voltage to a mechanical actuating force. The electroactive polymer is further configured to apply the actuating force to the ring deployment mechanism to deploy the anastomotic ring.

20 Claims, 12 Drawing Sheets

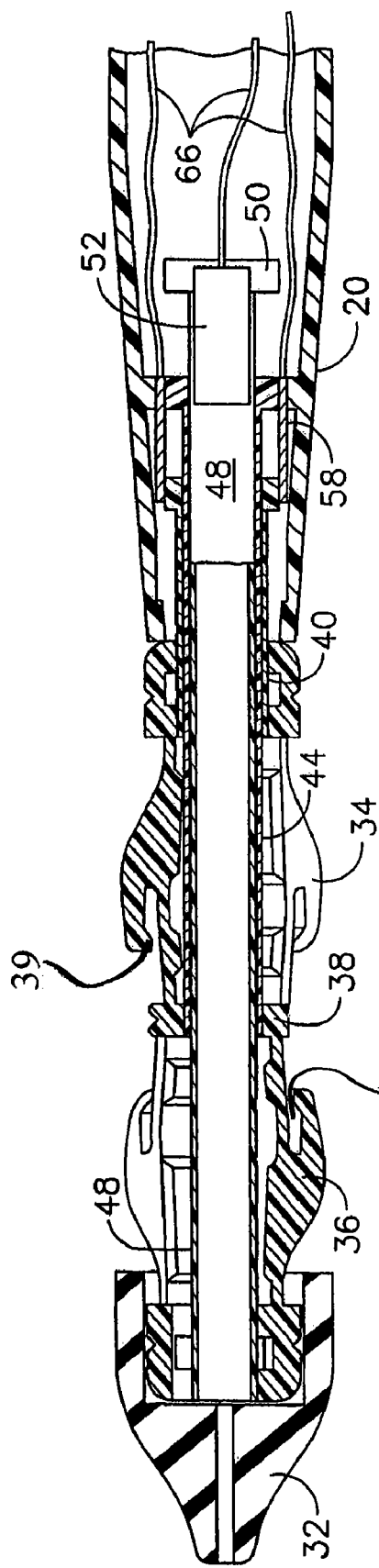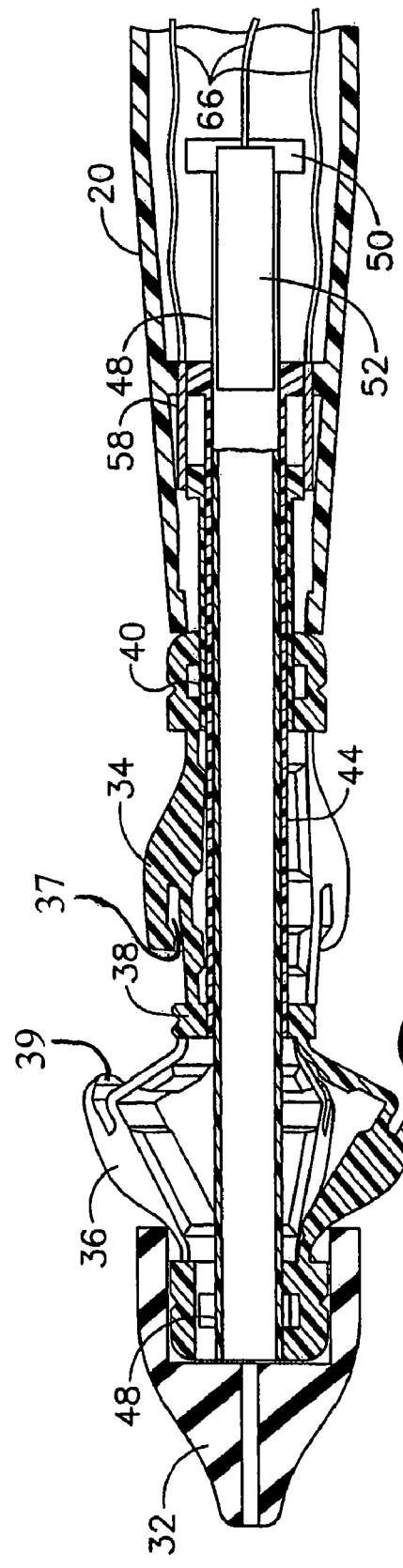

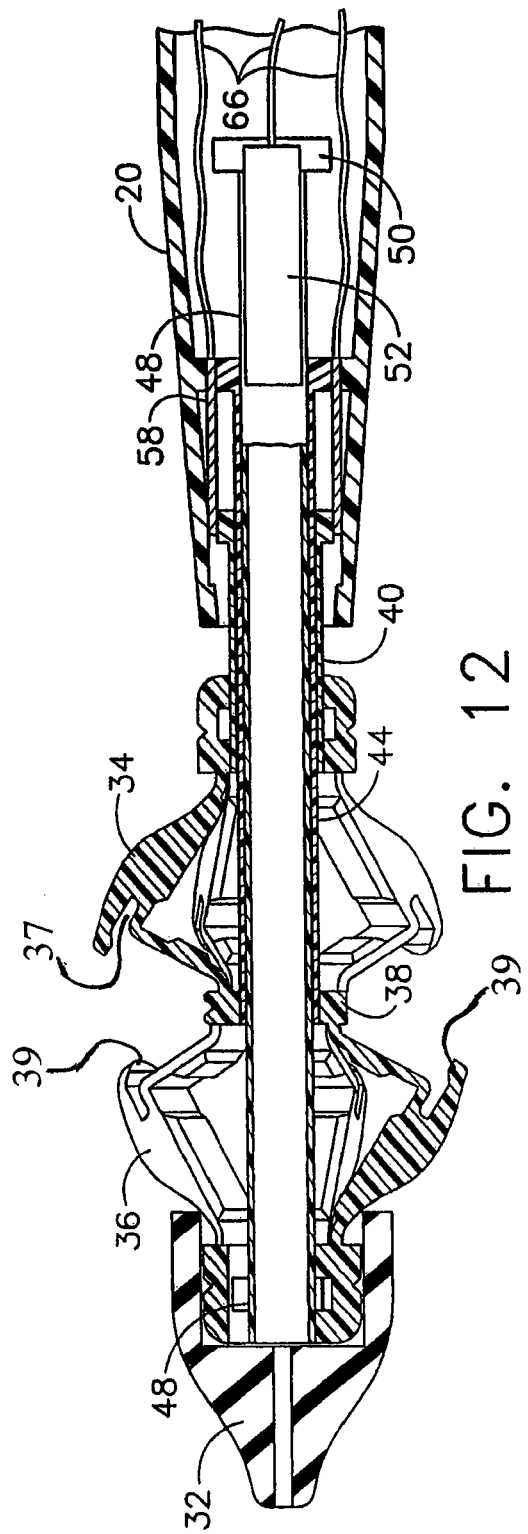
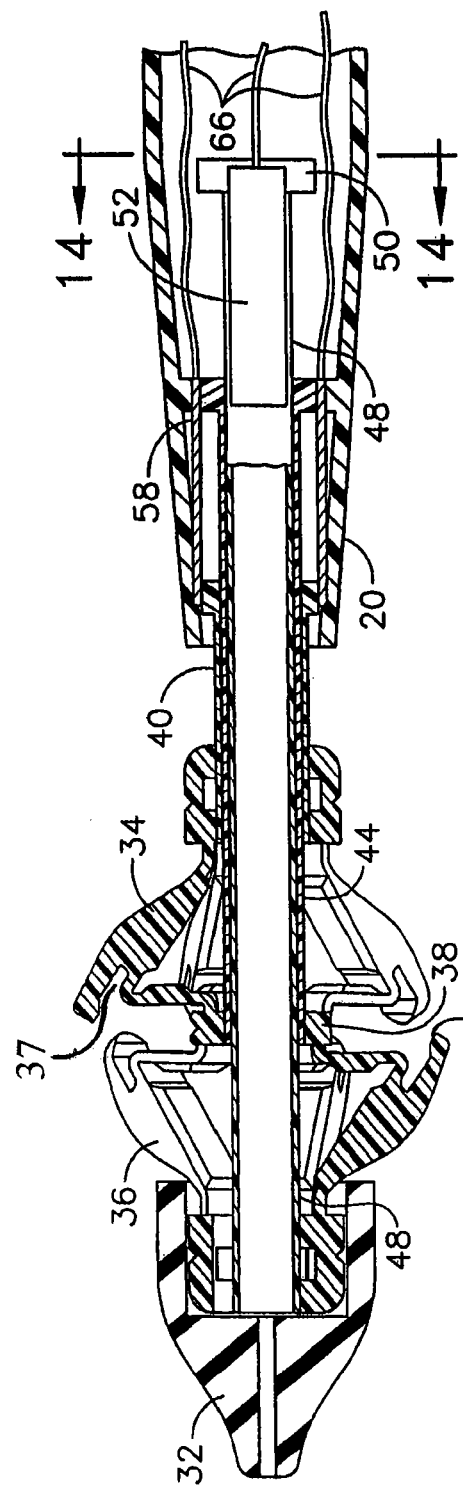
FIG. 12
FIG. 13

ANASTOMOTIC RING APPLIER DEVICE UTILIZING AN ELECTROACTIVE POLYMER

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

Many conventional applier devices require that an actuation force be transmitted from the operating handle to the distal ring deployment mechanism. While this force is generally relatively small, even a low force may be prohibitive when it must be transmitted to the end of a long flexible or detached structure. Consequently, it may be desirable to have an anastomotic ring applier device in which an actuation force capable of deploying an anastomotic ring is generated at a distal portion of the device and is independent of the length of the shaft connecting the operating handle to the ring deployment mechanism.

BRIEF SUMMARY OF THE INVENTION

Various embodiments of the invention provide an anastomotic ring applier device that allows the surgeon to cause an actuation force to generate at a distal portion of the applier device in order to actuate a ring deployment mechanism to deploy an anastomotic ring.

In one embodiment, an anastomotic ring applier device comprises a ring deployment mechanism configured to receive and deploy an anastomotic ring. The device further comprises a power source capable of generating a voltage. The device also comprises an electroactive polymer adapted to receive voltage and convert it into a mechanical actuation force. The electroactive polymer is further adapted to apply the mechanical actuation force to the ring deployment mechanism in order to deploy the ring. This device provides a means of generating a mechanical actuation force capable of deploying an anastomotic ring that is not necessarily dependent on transmitting a mechanical force over a long distance.

In another embodiment, an instrument comprises a handle including an actuating member for receiving operator input. The device further comprises an electroactive polymer that is adapted to receive operator input in the form of voltage. The electroactive polymer is further be adapted to convert voltage to a mechanical actuation force, which it may apply to a ring deployment mechanism to apply an anastomotic ring. In this embodiment, the device allows the operator to apply a negligible force to an actuating member to generate an electrical current to produce the necessary mechanical actuation force at the ring deployment mechanism.

In yet another embodiment, a device comprises a handle connected to a proximal portion of an elongated shaft. The device further comprises a ring deployment mechanism at a distal end of the shaft. The device includes a power source adapted to generate a voltage, which may be received by an electroactive polymer. The electroactive polymer is adapted to convert the voltage to a mechanical actuation force, which it may apply to the ring deployment mechanism to apply an anastomotic ring. In this embodiment, the device may advantageously avoid the need to transmit a mechanical actuation force along the entire length of an elongated shaft.

In still another embodiment, the device comprises a handle and an elongated shaft comprising a proximal portion and a distal portion, wherein the proximal portion of the shaft is connected to the handle. The device further comprises a ring deployment mechanism at a distal portion of the shaft. The ring deployment mechanism comprises a proximal portion and a distal portion. A first electroactive polymer is connected to the proximal portion of the deployment mechanism, and is further adapted to receive voltage from the power source and convert it to a mechanical actuation force that may be applied to the proximal portion of the deployment mechanism to deploy a proximal portion of the anastomotic ring. Similarly, a second electroactive polymer is connected to the distal portion of the deployment mechanism, and is further adapted to receive voltage from the power source and convert it to a mechanical actuation force that may be applied to the distal portion of the deployment mechanism to deploy a distal portion of the anastomotic ring. In this embodiment, the device may advantageously generate separate mechanical actuation forces to deploy two portions of an anastomotic ring without requiring that mechanical force be necessarily transmitted along the length of a shaft.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

FIG. 10 is a cross-sectional view of the ring deployment mechanism of FIG. 8 in an unactuated position.

FIG. 11 is a cross-sectional view of the ring deployment mechanism of FIG. 8 with the distal portion in a partially actuated position.

FIG. 12 is a cross-sectional view of the ring deployment mechanism of FIG. 8 with both the distal and the proximal portions in a partially actuated position.

FIG. 13 is a cross-sectional view of the ring deployment mechanism of FIG. 8 with both the distal and the proximal portions in a fully actuated position.

DETAILED DESCRIPTION OF THE INVENTION

Figure 1:
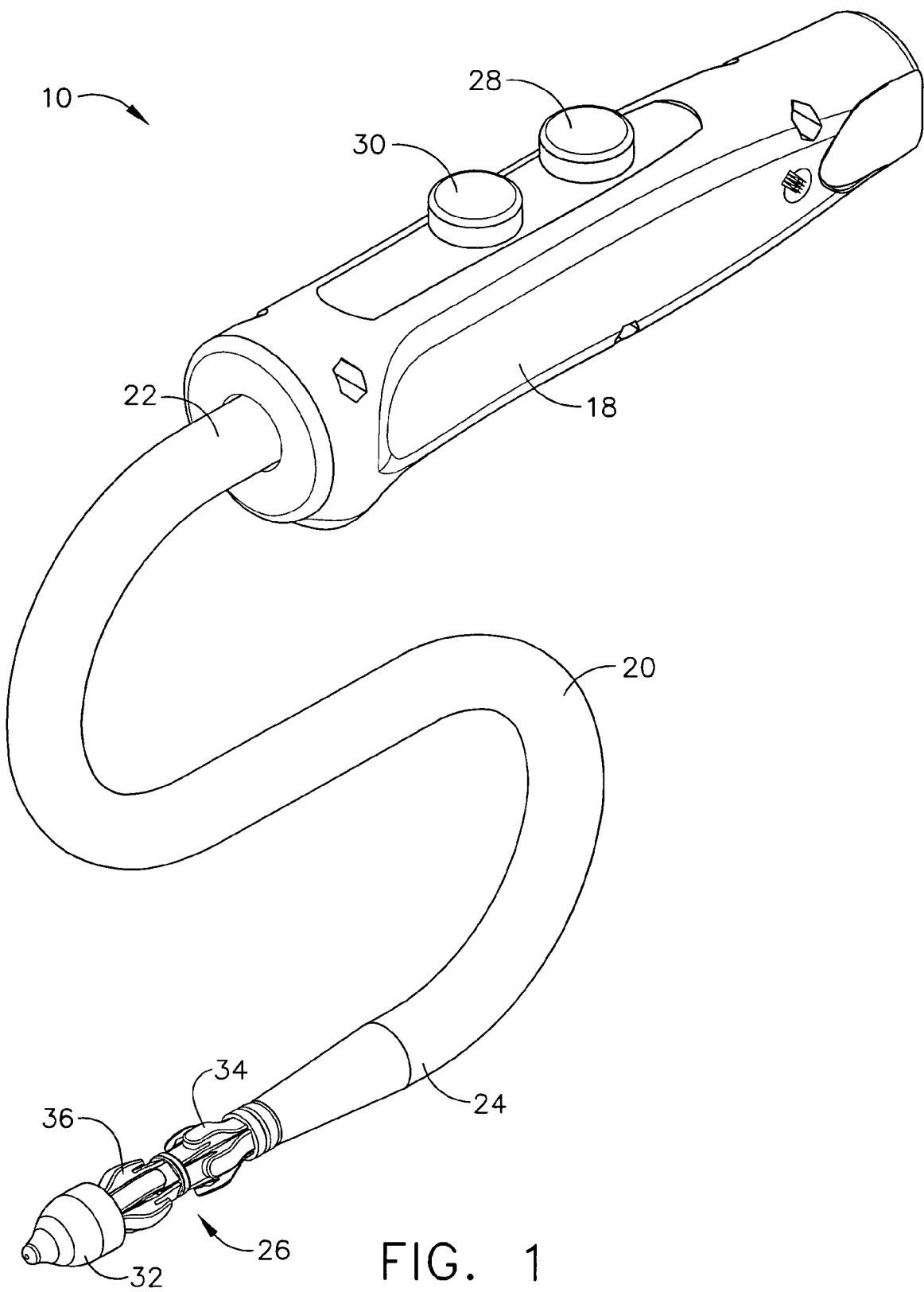
FIG. 1 is a perspective view of an anastomotic ring applier device.
Figure 2:
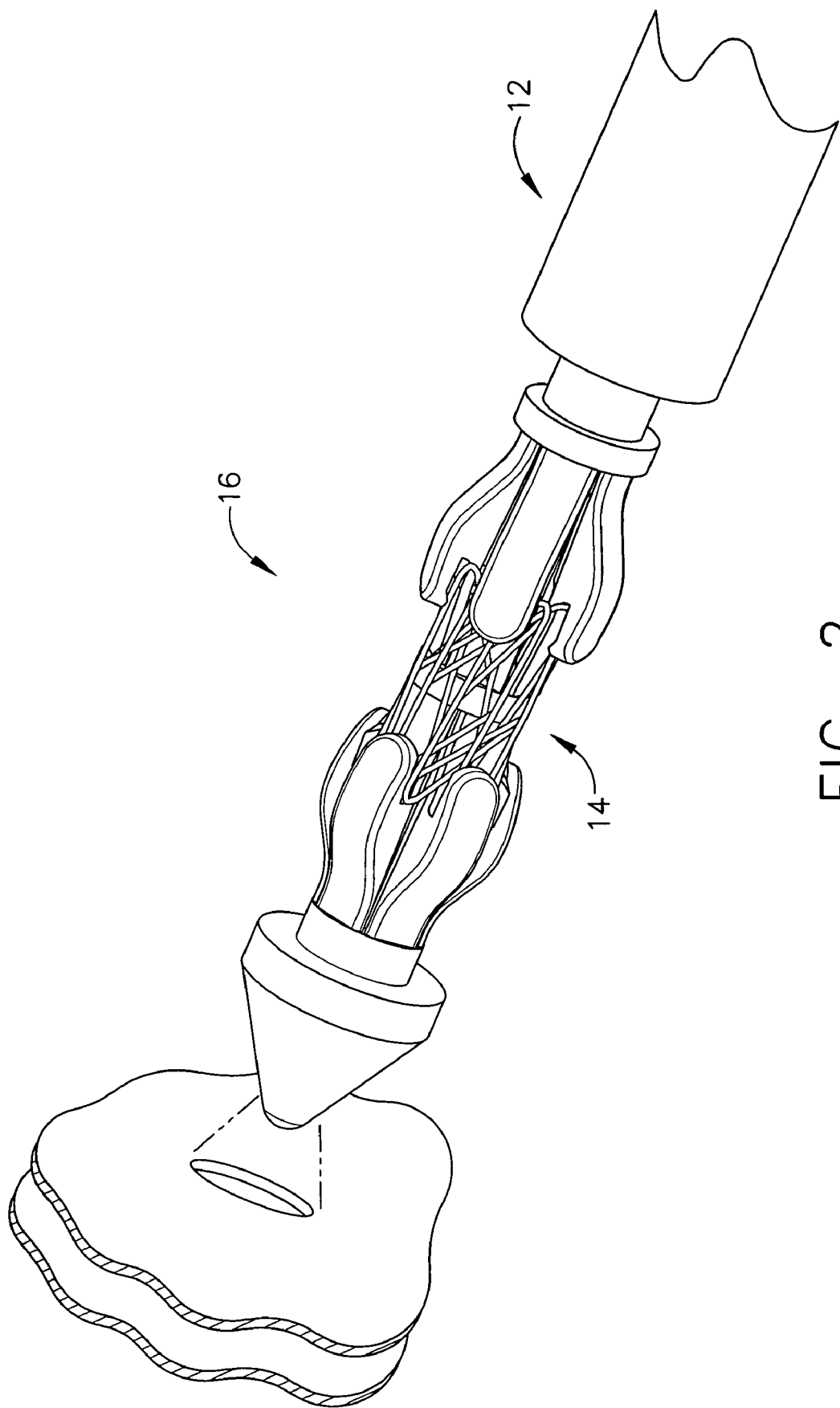
FIG. 2 is a partial perspective view of the distal portion of an anastomotic ring applier device holding an anastomotic ring in an unactuated position.
Figure 3:
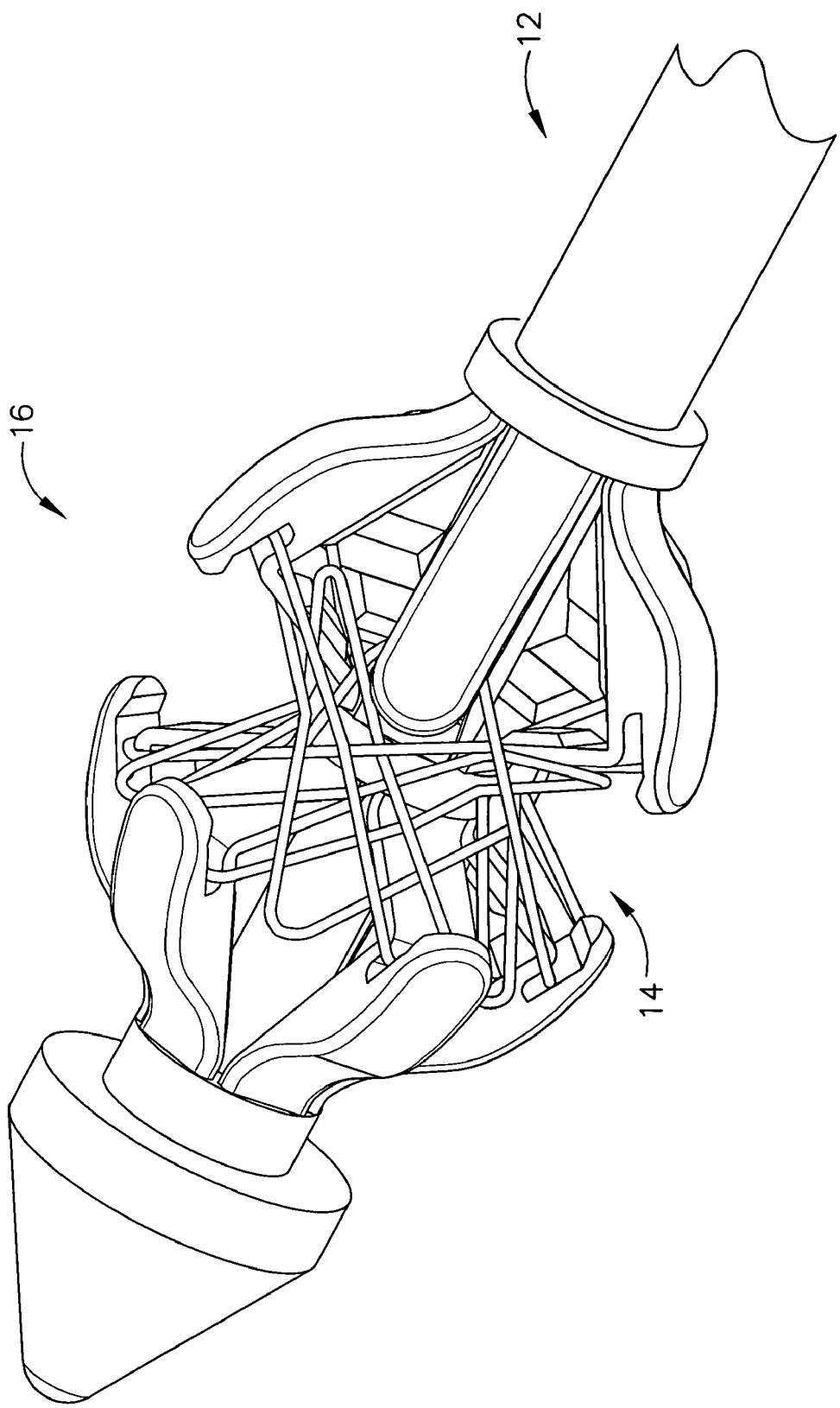
FIG. 3 is a partial perspective view of the anastomotic ring applier device of FIG. 2 holding an anastomotic ring in a partially actuated position.
Figure 4:
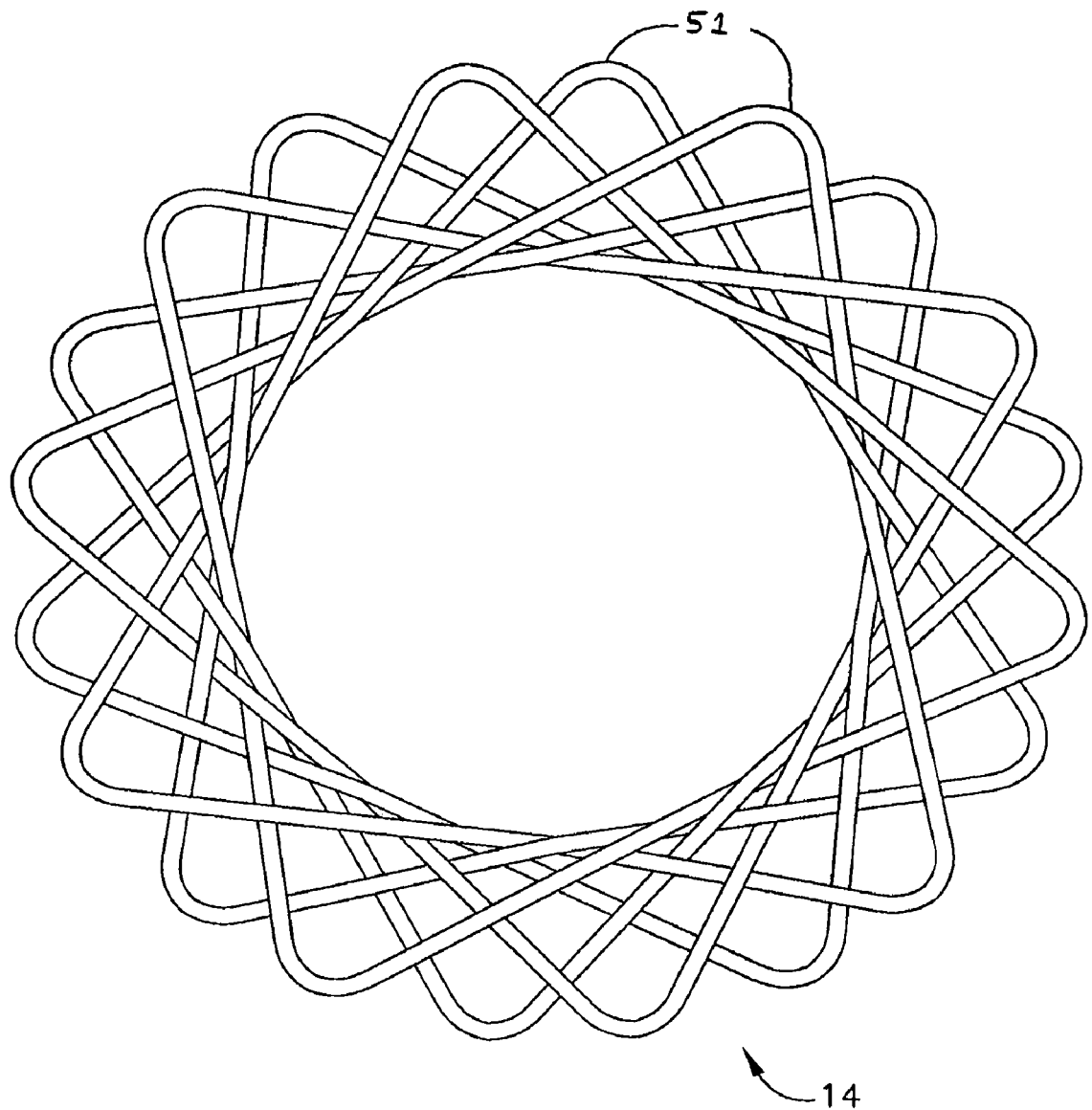
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring again to FIG. 1, applier 10 of the present example comprises a handle 18 connected to an elongated shaft 20 having a proximal end 22 and a distal end 24. As shown in FIG. 1, elongated shaft 20 is flexible, either along its entire length or at one or more joints. Of course, shaft 20 may alternatively be rigid, resilient, malleable, or have other properties. Distal end 24 of shaft 20 comprises a ring deployment mechanism 26. Deployment mechanism 26 may be actuated by a button or lever located on handle 18. As shown in FIG. 1, in one embodiment, handle 18 comprises a pair of actuator buttons 28, 30. The functioning of actuator buttons 28, 30 will be described below. Ring deployment mechanism 26 is located proximal of a tip 32.

Figure 5:
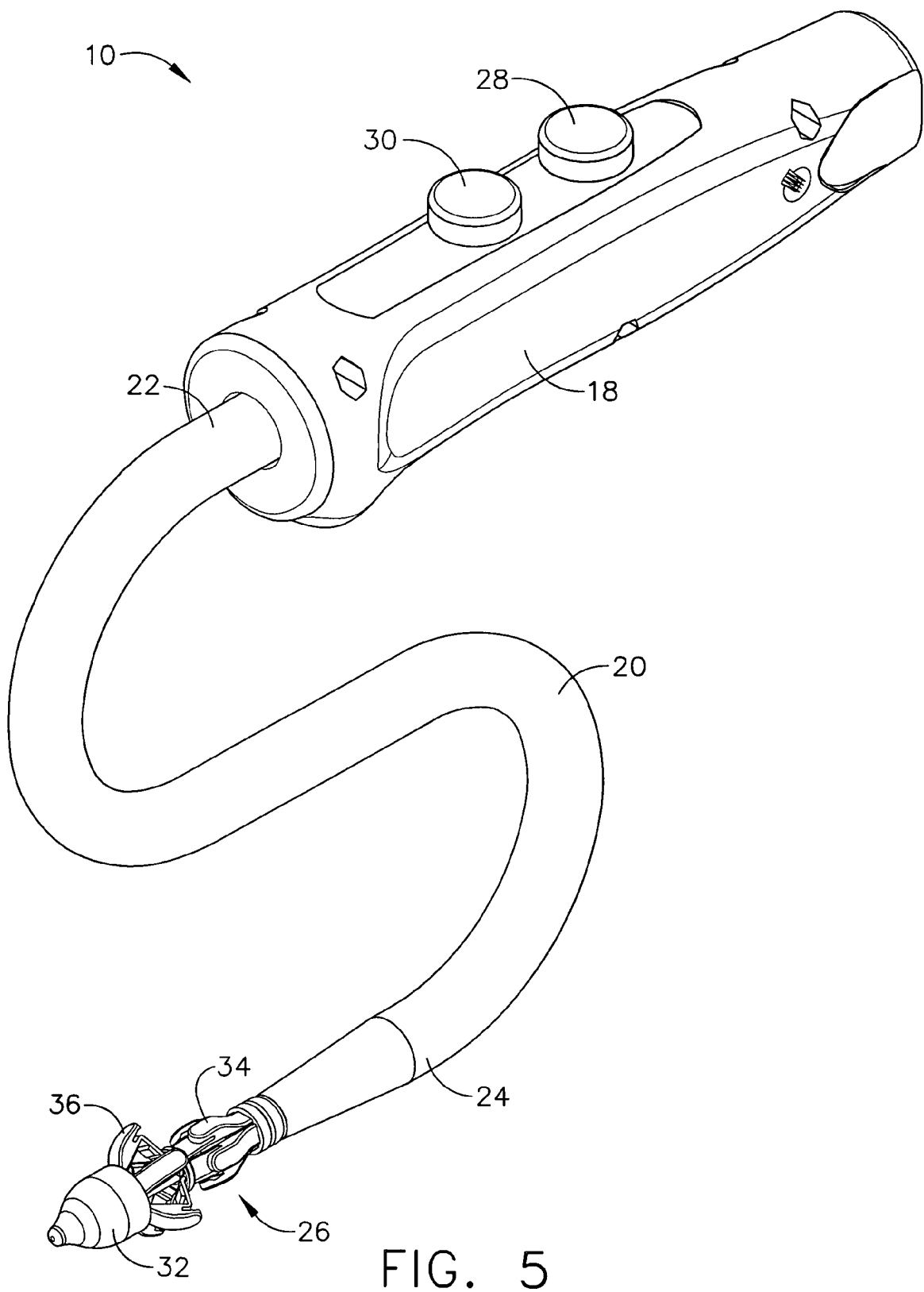
FIG. 5 is a perspective view of the device of FIG. 1 with a distal portion of a ring deployment mechanism in a partially actuated position.
Figure 6:
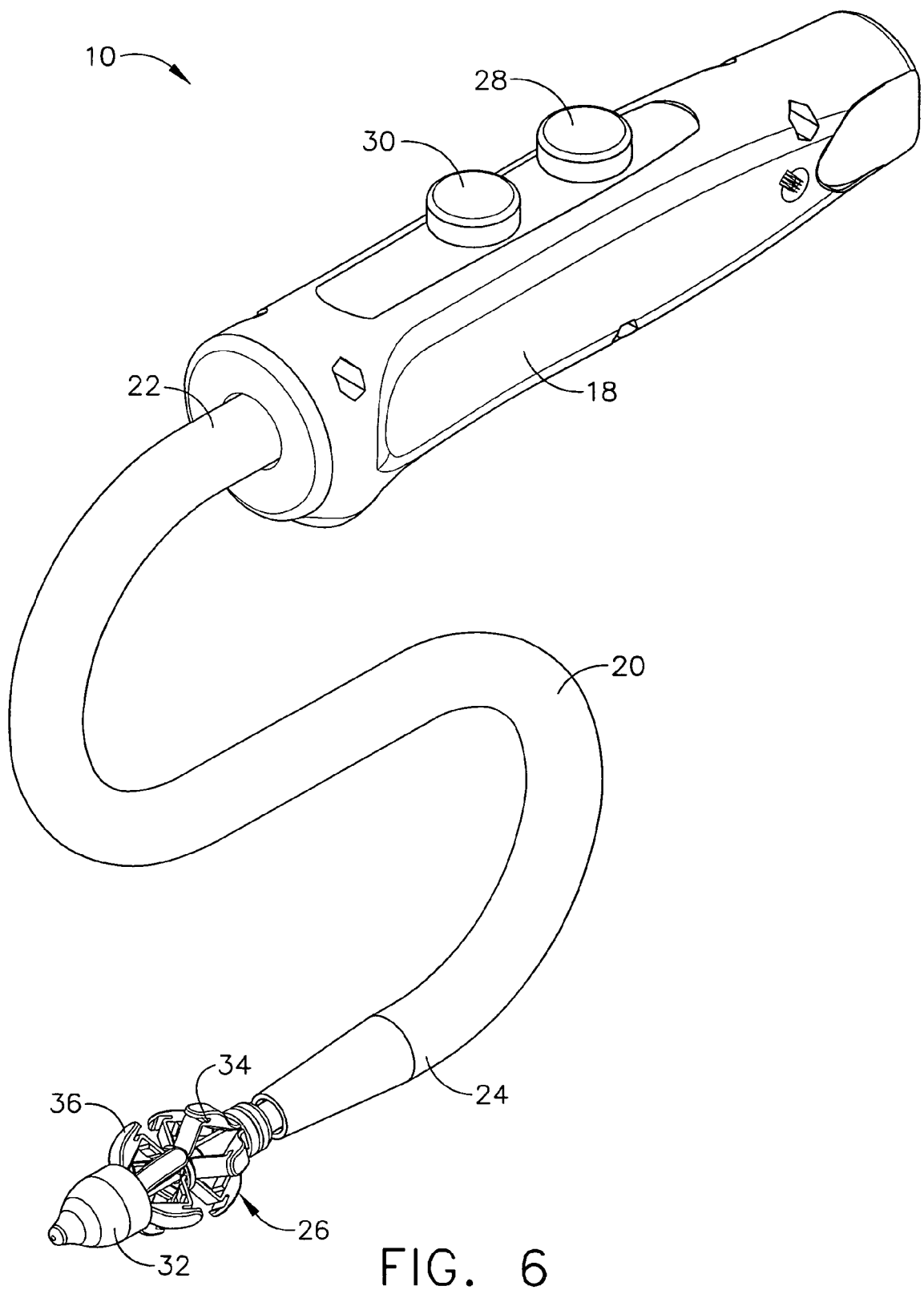
FIG. 6 is a perspective view of the device of FIG. 1 shown with both a distal and a proximal portion of a ring deployment mechanism in a partially actuated position.
Figure 7:
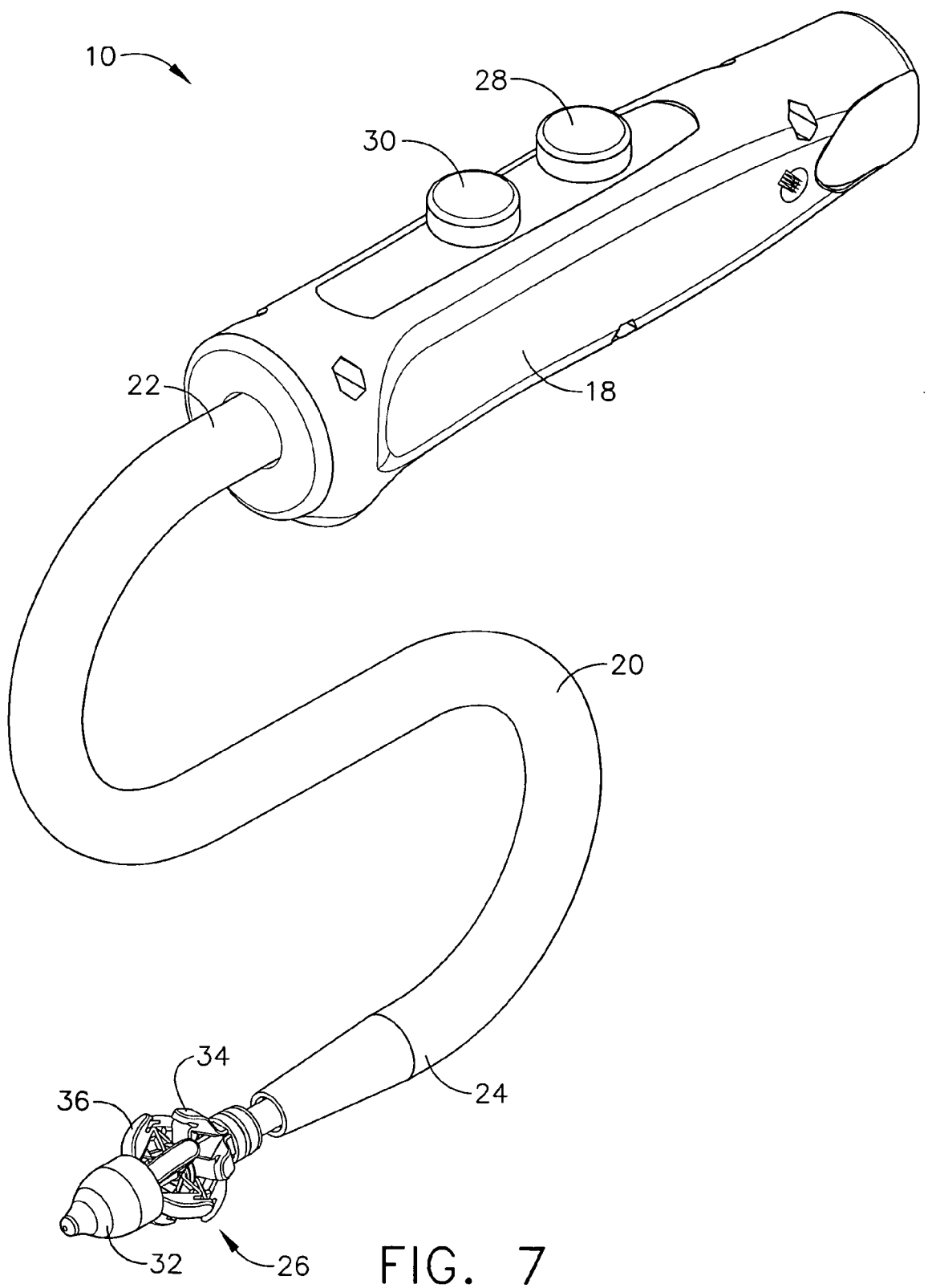
FIG. 7 is a perspective view of the device of FIG. 1 shown with both a distal and a proximal portion of a ring deployment mechanism in a fully actuated position.

In the present example, ring deployment mechanism 26 comprises a plurality of proximal fingers 34 and a plurality of distal fingers 36. Both proximal fingers 34 and distal fingers 36 are each in a double-hinged relationship with a stationary mid-ring 38 of ring deployment mechanism 26. Proximal fingers 34 are adapted to slide toward mid-ring 38 in response to actuation of actuator button 28, causing fingers 34 to actuate outwardly from shaft 20 (FIGS. 6 and 7). Likewise, distal fingers 36 are adapted to slide toward mid-ring 38 in response to actuation of actuator button 30, causing fingers 36 to actuate outwardly from shaft 20 (FIGS. 5 and 7). In this manner, an anastomotic ring may be deployed from the compressed, cylindrical position to the actuated, hollow rivet-forming position, as shown in FIG. 3. Fingers 34, 36 are configured to hold the anastomotic ring by engaging petals 51 prior to and during deployment of the anastomotic ring, and release petals 51 upon deployment of the anastomotic ring. In the illustrated version, fingers 34, 36 each comprise a gripping slot 37 and an inwardly directed retention tip 39 adjacent to each gripping slot 37.

Figure 8:
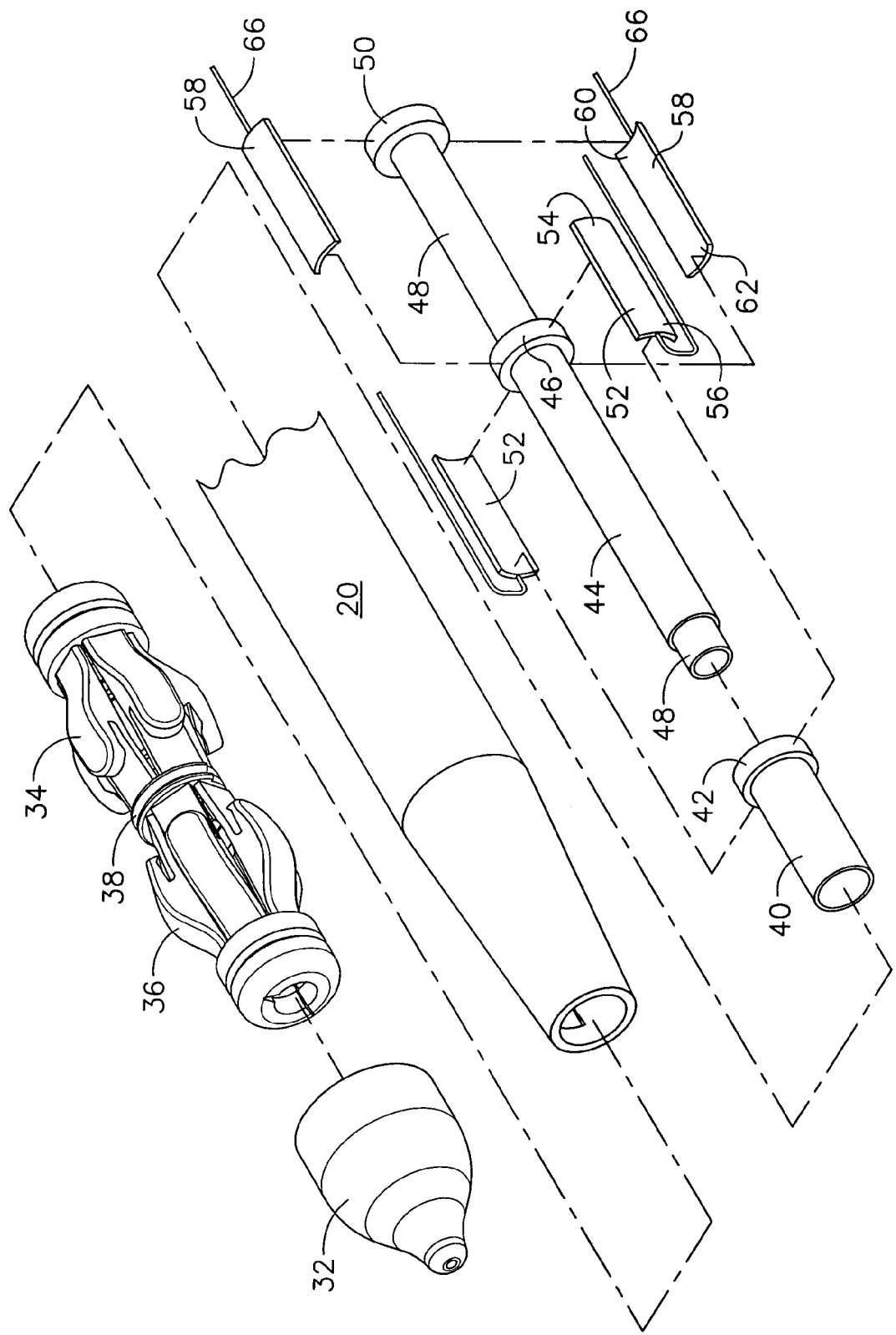
FIG. 8 is an exploded view of the ring deployment mechanism of the device of FIG. 1.

Referring to FIG. 8, an embodiment of ring deployment mechanism 26 is shown in an exploded view. As described above, ring deployment mechanism 26 comprises proximal fingers 34. Proximal fingers 34 are connected to an outer tube 40 comprising a flange 42. Mid-ring 38 is connected to a ground tube 44 comprising a flange 46. Distal fingers 36 are connected to an inner tube 48 comprising a flange 50. Ground tube 44 is grounded to shaft 20, as shown in FIGS. 10-13, and is therefore stationary. Other suitable configurations for ring deployment mechanism 26 will be apparent to those of ordinary skill in the art.

Figure 14:
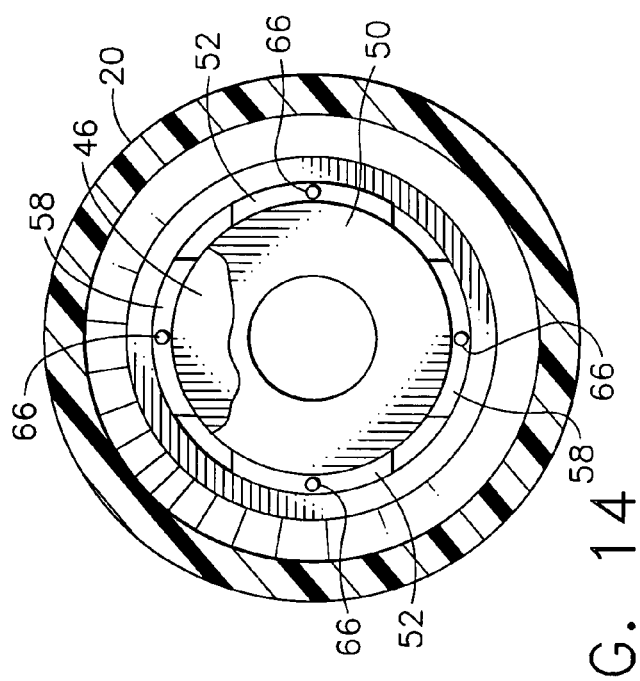
FIG. 14 is a cross-sectional view of a shaft portion of an anastomotic ring applier device consistent with the present invention, taken along Plane 14 of FIG. 13.

In the present example, ring deployment mechanism 26 further comprises an electroactive polymer (EAP) 52 comprising a proximal portion 54 and a distal portion 56. Proximal portion 54 of EAP 52 is attached to flange 46 of ground tube 44. Distal portion 56 is attached to flange 42 of outer tube 40. As shown in FIG. 8 and FIG. 14, applier 10 comprises a pair of opposing EAPs 52. An EAP 58 comprising a proximal portion 60 and a distal portion 62 is further included in ring deployment mechanism 26. Proximal portion 60 is attached to flange 50 of inner tube 48 and distal portion 62 is attached to flange 46 of ground tube 44. As shown in FIG. 8 and FIG. 14, applier 10 comprises a pair of such EAPs 58. EAPs may be of any suitable type, including but not limited to electronic EAPs or ionic EAPs.

In the present example, EAPs 52, 58 comprise thin conductive sheets laminated onto a polymer core. In one embodiment, the conductive sheets comprise a carbon fiber composite. When a small voltage is induced across the electrodes of EAPs 52, 58, the electrodes are drawn together, resulting in a deformation of the polymer substrate. Deformation of the substrate causes the polymer to expand in one direction and to contract in the perpendicular direction. The voltage necessary to cause deformation of the polymer substrate may be relatively small. In one embodiment, the voltage induced across the electrodes of the EAPs may be between approximately 1.5 volts to approximately 3 volts. Alternatively, EAPs may be configured to be responsive to other voltages. It is also possible to stack EAP sheets in order to achieve an additive effect in generating force. In one embodiment, EAP sheets are very thin in order to optimize output force. By way of example only, the thickness of the EAP sheets may be approximately 20 microns, resulting in an available power density of approximately 200 kg/cm², or about 100 times the power density of human muscle, and a maximum tensile strength of 100 MPa (or 60 MPa using engineering plastics). The EAPs may be capable of achieving a maximum strain of 40% at a maximum strain rate of 8% per second. It will be appreciated, however, that the foregoing EAP properties are merely exemplary and thus optional, and a variety of other EAP configurations may be used, as well as EAPs having a variety of other properties.

FIG. 10 shows proximal and distal fingers 34, 36 in an unactuated state. By attaching EAP 58 to slideable inner tube 48 and stationary ground tube 44, EAP 58 of the present example is adapted to expand in response to voltage and thereby draw distal fingers 36 proximally and outwardly FIGS. 11-13), thereby deploying a distal portion of an anastomotic ring. Similarly, by fixedly attaching EAP 52 to ground tube 44 and outer tube 40, EAP 52 is adapted to expand longitudinally in response to induction of voltage and thereby push proximal fingers 34 distally and outwardly (FIGS. 12-13), deploying a proximal portion of an anastomotic ring.

Figure 9:
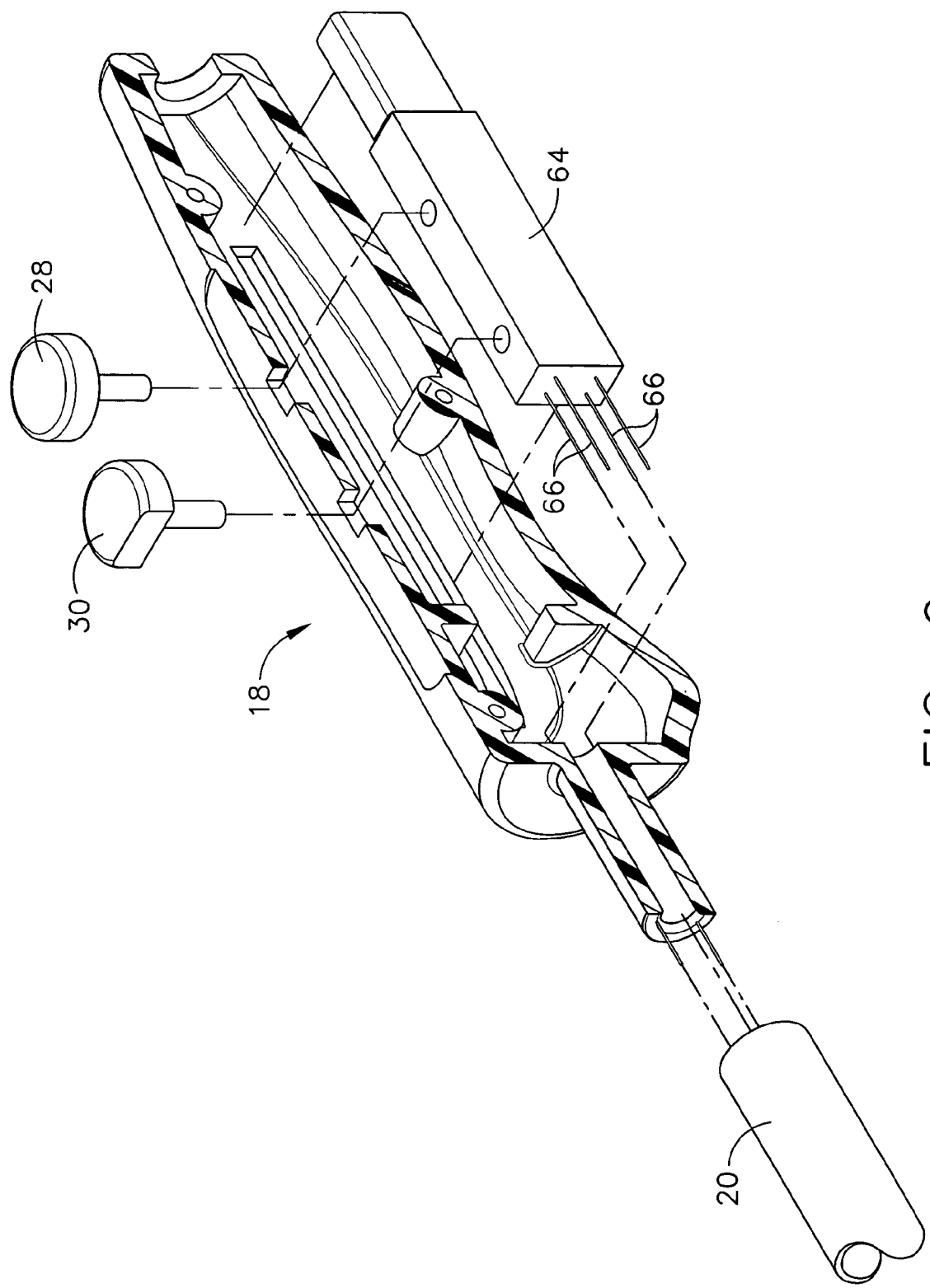
FIG. 9 is a cross-sectional exploded view of the handle of the device of FIG. 1, omitting a left half of the handle.
Figure 15:
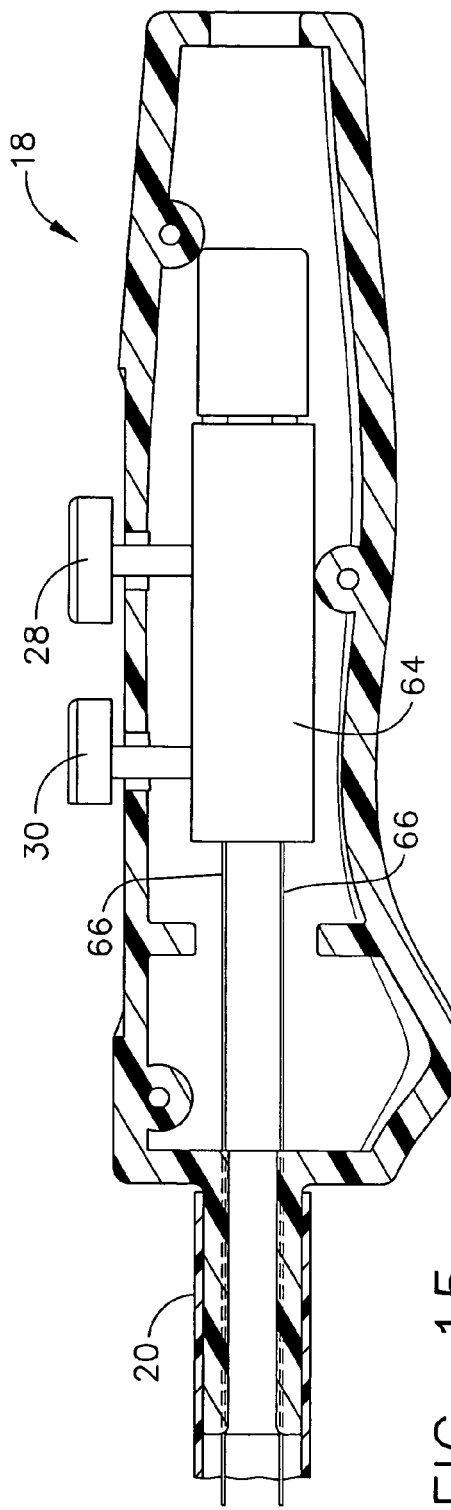
FIG. 15 is a cross-sectional view of the handle of the device of FIG. 1, omitting a left half of the handle.

As shown in FIG. 9 and 15, handle 18 houses a power source 64. Alternatively, an external power source may be utilized to induce a voltage across EAPs 52, 58. In the present example, first actuator button 28 is moveable from a first, non-actuated position to a second, actuated position, thereby causing power source 64 to induce a voltage across EAP 52, causing the polymer substrate to expand and push proximal fingers 34 distally to deploy a proximal portion of an anastomotic ring. Second actuator button 30 is moveable from a first, non-actuated position to a second, actuated position, thereby causing power source 64 to induce a voltage across EAP 58, causing the polymer substrate to expand and draw distal fingers 36 proximally to deploy a distal portion of an anastomotic ring. Alternatively, the relationship between actuator buttons 28, 30 and fingers 34, 36 may be reversed, such that first actuator button 28 controls distal fingers 36 and second actuator button 30 controls proximal fingers 34. In addition, any suitable alternative to actuator buttons 28, 30 may be used. Other variations will be apparent to those of ordinary skill in the art.

In the present example, when first and second actuator buttons 28, 34 are in the unactuated position, applier 10 is configured such that no voltage is induced across EAPs 52, 58. In the present example, voltage is conducted to EAPs 52, 58 from power source 64 via conductive wires 66. Each EAP 52, 58 is adapted to receive a positive and negative lead 66 from power source 64.

While the foregoing examples include EAPs being connected to ground tube 44, inner tube 48, and outer tube 40, it will be appreciated that EAPs may be used in a device such as applier 10 to deploy an anastomotic ring in a variety of other ways and configurations. By way of example only, instead of being connected to tubes 44, 48, and 40, EAPs may be connected to one or more fingers 34, 32 to accomplish actuation of the fingers 34, 32. Alternatively, at least a portion of one or more fingers 34, 32 may comprise EAP material. For instance, at least a portion of at least one side of each finger 34, 32 may comprise EAP material. Thus, fingers 34, 32 may be configured with EAP such that they operate in a manner similar to a venus flytrap. In other words, fingers 34, 32 may open to deploy an anastomotic ring by having the surface area of one side of a finger/leaf increase relative the surface area of the other side of the finger/leaf. By way of example only, at least a portion of fingers 34, 32 may comprise an EAP configured to expand in response to an applied voltage, thereby causing fingers 34, 32 to expand for ring deployment. Similarly, at least a portion of fingers 34, 32 may comprise an EAP configured to shrink or retract in response to an applied voltage (or in the absence of an applied voltage), thereby causing fingers 34, 32 to retract or close for removal of applier 10. Alternatively, EAP may be configured such that it causes fingers 34, 32 to retract or close when polarity of the voltage is reversed. In such an embodiment, the applier 10 may include a switch or other means for switching polarity.

Alternatively, fingers 34, 32 may comprise an EAP and a resilient material, such that fingers 34, 32 open in response to voltage being applied to EAP, and fingers 34, 32 close at the urging of resilient material when voltage is removed. In yet another embodiment, each finger 34, 32 is hingedly connected to a linkage comprising EAP. Other suitable ways in which fingers 34, 32 may be configured with EAP materials will be apparent to those of ordinary skill in the art.

It will also be appreciated that, where EAP is positioned in ring deployment mechanism 26 at a location distally beyond shaft 20, one or more of tubes 44, 48, or 40 may be obsolete. In one embodiment, where EAP is positioned in ring deployment mechanism 26 at a location distally beyond shaft 20, tubes 44, 48, or 40 are absent from shaft 20, and shaft 20 houses conductive wires 66 only. Alternatively, EAP may be used both within shaft 20 and distally beyond shaft 20. Still other suitable configurations will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for implanting an anastomotic ring device, comprising:
   (i) a ring deployment mechanism configured to receive and deploy an anastomotic ring under a mechanical actuation force, the anastomotic ring comprising a first plurality of petals and a second plurality of petals, wherein the ring deployment mechanism comprises a plurality of distal fingers, a plurality of proximal fingers, and a central member positioned longitudinally between the plurality of distal fingers and the plurality of proximal fingers, wherein each distal finger comprises a proximal segment and a distal segment, wherein the proximal segment of each distal finger is hingedly connected at a first end to a corresponding distal segment of each distal finger and hingedly connected at a second end to the central member, wherein the distal segment of each distal finger is hingedly connected at a first end to a corresponding proximal segment of each distal finger and hingedly connected at a second end to a distal portion of the ring deployment mechanism, wherein the distal segment of each distal finger comprises an integral gripping slot, wherein each gripping slot of each distal finger is configured to receive a respective petal of the first plurality of petals of the anastomotic ring, wherein each proximal finger comprises a proximal segment and a distal segment, wherein the distal segment of each proximal finger is hingedly connected at a first end to a corresponding proximal segment of each proximal finger and hingedly connected at a second end to the central member, wherein the proximal segment of each proximal finger is hingedly connected at a first end to a corresponding distal segment of each proximal finger and hingedly connected at a second end to a proximal portion of the ring deployment mechanism, wherein the proximal segment of each proximal finger comprises an integral gripping slot, wherein each gripping slot of each proximal finger is configured to receive a respective petal of the second plurality of petals of the anastomotic ring, wherein the central member longitudinally separates the proximal segments of the distal fingers from the distal segments of the proximal fingers;

(ii) a power source for generating voltage; and (iii) an electroactive polymer in communication with the ring deployment mechanism and operatively configured to produce the mechanical actuation force in response to the generated voltage.

2. The surgical instrument of claim 1, wherein the power source comprises a battery.

3. The surgical instrument of claim 1, wherein the electroactive polymer comprises a conductive material applied to a polymer substrate.

4. The surgical instrument of claim 3, wherein the polymer substrate is configured to expand in one direction and contract in a perpendicular direction in response to inducement of voltage across the electroactive polymer.

5. The surgical instrument of claim 1, further comprising an actuator moveable from a first, unactuated position to a second, actuated position, wherein the actuator is operable to cause the power source to induce voltage across the electroactive polymer at the second, actuated position.

6. The surgical instrument of claim 1, wherein the ring deployment mechanism comprises a proximal portion and a distal portion, wherein the electroactive polymer is configured to communicate actuating force to the proximal portion of the ring deployment mechanism.

7. The surgical instrument of claim 6, further comprising a second electroactive polymer.

8. The surgical instrument of claim 7, wherein the second electroactive polymer is configured to communicate actuating force to the distal portion of the ring deployment mechanism.

9. The surgical instrument of claim 8, further comprising a second actuator moveable from a first, unactuated position to a second, actuated position, wherein the second actuator is operable to cause the power source to induce voltage across the second electroactive polymer at the second, actuated position.

10. The surgical instrument of claim 1, wherein the electroactive polymer comprises a plurality of electroactive polymer sheets stacked atop one another to generate an additive force.

11. A surgical instrument for implanting an anastomotic ring device, comprising:

(i) a handle;

(ii) an elongate shaft comprising a proximal portion and a distal portion, the proximal portion being connected to the handle;

(iii) a ring deployment mechanism located on the distal portion of the elongate shaft, the ring deployment mechanism comprising (a) a proximal portion and a distal portion responsive respectively to opposing distal and proximal mechanical actuation forces, and (b) a plurality of fingers configured to receive an anastomotic ring, the anastomotic ring having a plurality of petals, the fingers being moveable from a first position longitudinally aligned with the elongate shaft to a second position in which the fingers actuate outwardly from a longitudinal axis of the elongate shaft to actuate at least a portion of an anastomotic ring, wherein each finger comprises a gripping slot, wherein each gripping slot of each finger is configured to receive a respective petal of the anastomotic ring, wherein each gripping slot is oriented substantially parallel with the longitudinal axis of the elongate shaft when the ring deployment mechanism is in an unactuated position, wherein the gripping slots open in a longitudinal direction substantially parallel to the axis of the elongate shaft when the ring deployment mechanism is in an unactuated position, wherein the number of gripping slots is equivalent to the number of fingers, wherein each of the plurality of fingers further comprises an inwardly directed retention tip adjacent to each gripping slot;

(iv) a power source operatively configured to generate voltage;

(v) a first electroactive polymer connected to the proximal portion of the ring deployment mechanism and operatively configured to produce the distal mechanical actuation force in response to the generated voltage; and (vi) a second electro active polymer connected to the distal portion of the ring deployment mechanism and operatively configured to produce the proximal mechanical actuation force in response to the generated voltage.

12. The surgical instrument of claim 11, wherein the power source is housed in the handle.

13. The surgical instrument of claim 11, wherein the ring deployment mechanism further comprises a central portion attached to a stationary first tube.

14. The surgical instrument of claim 11, wherein the proximal portion of the ring deployment mechanism is attached to a first end of the first electroactive polymer by a first tube slideably contained within the shaft, wherein the first electroactive polymer is further attached at a second end of the first electroactive polymer to a stationary element of the surgical instrument.

15. The surgical instrument of claim 14, wherein inducement of voltage across the first electroactive polymer is configured to cause the first tube to move distally, forcing the proximal portion of the ring deployment mechanism distally.

16. The surgical instrument of claim 14, wherein the distal portion of the ring deployment mechanism is attached to a first end of the second electroactive polymer by a second tube slideably contained within the shaft, wherein the second electroactive polymer is further attached at a second end of the second electroactive polymer to a stationary element of the surgical instrument.

17. The surgical instrument of claim 16, wherein inducement of voltage across the second electroactive polymer is configured to cause the second tube to move proximally, forcing the distal portion of the ring deployment mechanism proximally.

18. The surgical instrument of claim 11, wherein the proximal portion of the ring deployment mechanism is associated with at least one of the plurality of fingers, wherein the at least one of the plurality of fingers is configured to move distally and articulate outwardly in response to the actuation force.

19. The surgical instrument of claim 11, wherein the distal portion of the ring deployment mechanism is associated with at least one of the plurality of fingers, wherein the at least one of the plurality of fingers is configured to move proximally and articulate outwardly in response to the actuation force.

20. A surgical instrument for implanting an anastomotic ring device, comprising:
(i) a handle;
(ii) an elongate shaft comprising a proximal portion and a distal portion, the proximal portion being connected to the handle;
(iii) a ring deployment mechanism configured to receive and deploy the anastomotic ring, the anastomotic ring having a plurality of petals, wherein the ring deployment mechanism comprises a plurality of distal fingers, a plurality of proximal fingers, and a central member positioned longitudinally between the plurality of distal fingers and the plurality of proximal fingers, wherein each distal finger comprises a proximal segment and a distal segment, wherein the proximal segment of each distal finger is hingedly connected at a first end to a corresponding distal segment of each distal finger and hingedly connected at a second end to the central member, wherein the distal segment of each distal finger is hingedly connected at a first end to a corresponding proximal segment of each distal finger and hingedly connected at a second end to a distal portion of the ring deployment mechanism, wherein the proximal segment of each distal finger extends radially inward from the corresponding distal segment of each distal finger toward the central member when the ring deployment mechanism is in an actuated position, wherein the distal segment of each distal finger comprises an integral gripping slot, wherein each gripping slot of each distal finger is configured to receive a respective petal of the anastomotic ring, wherein each proximal finger comprises a proximal segment and a distal segment, wherein the distal segment of each proximal finger is hingedly connected at a first end to a corresponding proximal segment of each proximal finger and hingedly connected at a second end to the central member, wherein the proximal segment of each proximal finger is hingedly connected at a first end to a corresponding distal segment of each proximal finger and hingedly connected at a second end to a proximal portion of the ring deployment mechanism, wherein the distal segment of each proximal finger extends radially inward from the corresponding proximal segment of each distal finger toward the central member when the ring deployment mechanism is in an actuated position, wherein the proximal segment of each proximal finger comprises an integral gripping slot, wherein each gripping slot of each proximal finger is configured to receive a respective petal of the anastomotic ring, wherein the central member longitudinally separates the proximal segments of the distal fingers from the distal segments of the proximal fingers;
(iv) a power source adapted to generate voltage; and
(v) an electroactive polymer in communication with the ring deployment mechanism and adapted to receive voltage from the power source and convert it to mechanical actuation force, wherein the electroactive polymer is configured to communicate the mechanical actuation force to the ring deployment mechanism.

* * * * *